US005670138A

United States Patent [19]
Venema et al.

[11] Patent Number: 5,670,138
[45] Date of Patent: Sep. 23, 1997

[54] MOUTH-CARE PRODUCTS

[75] Inventors: Franciscus Ties Venema, Voorthuizen; Christiena Jannie Timmer, Amersfoort; Jolanda Douma, Amersfoort; Stephanus Aloysius Gerardus Jochems, Amersfoort, all of Netherlands

[73] Assignee: Sara Lee/DE N.V., Utrecht, Netherlands

[21] Appl. No.: 498,639

[22] Filed: Jul. 6, 1995

[30] Foreign Application Priority Data

Jul. 7, 1994 [EP] European Pat. Off. ............. 94201962

[51] Int. Cl.$^6$ ................ A61K 7/16; A61K 7/18; A61K 9/68; A61K 31/79
[52] U.S. Cl. ............... 424/52; 424/44; 424/49; 424/435; 424/440
[58] Field of Search ............... 424/49.58, 435, 424/440, 44

[56] References Cited

U.S. PATENT DOCUMENTS

| | | | |
|---|---|---|---|
| 3,956,480 | 5/1976 | Dichter et al. | 424/54 |
| 4,605,401 | 8/1986 | Chmelir et al. | 604/368 |
| 4,801,460 | 1/1989 | Goertz et al. | 424/465 |
| 4,880,660 | 11/1989 | Aasen et al. | 427/2 |
| 5,276,079 | 1/1994 | Duan et al. | 524/386 |
| 5,298,258 | 3/1994 | Akemi et al. | 424/484 |
| 5,362,420 | 11/1994 | Itoh et al. | 252/500 |
| 5,397,614 | 3/1995 | Patnode et al. | 428/40 |
| 5,408,022 | 4/1995 | Imazato et al. | 526/259 |
| 5,494,987 | 2/1996 | Imazato et al. | 526/263 |
| 5,534,198 | 7/1996 | Masters et al. | 510/182 |

FOREIGN PATENT DOCUMENTS

| | | |
|---|---|---|
| 333 301 | 3/1989 | European Pat. Off. . |
| 92 10992 | 12/1991 | European Pat. Off. . |
| 547665 | 6/1993 | European Pat. Off. . |

OTHER PUBLICATIONS

Abstracts of Goertz et al C.A. 108: 210215 of Ger DE 3612212(Oct. 1987).
Chmelir et al Derwent of EP 77510 (Apr. 1983) US 4605401(Aug. 1986).
Kawahara Derwent of JP 57 134407(Aug. 1982) U.S. 4689080(Aug. 1987).
Shah Derwent of 5B 2064 556 (Jun. 1981).
Itoh et al US PAT 94:97260 of U.S. 5362420 (Nov. 1994).
Aasen et al US PAT 89:92366 of U.S. 4880660 (Nov. 1989).
Goertz et al US PAT 89: 7426 of U.S. 4801460 (Jan. 1989).
Dichter et al US PAT 76:26337 of U.S. 3956480 (May 1976).

*Primary Examiner*—Shep K. Rose
*Attorney, Agent, or Firm*—Merchant, Gould, Smith, Edell, Welter & Schmidt, P.A.

[57] ABSTRACT

The invention is directed to improved mouth care products comprising an amount of at least one copolymer of N-vinylpyrrolidone and acrylic acid, in a weight ratio of 60-95 to 40-5, suitable additives and carrier material.

17 Claims, No Drawings

MOUTH-CARE PRODUCTS

The present invention is related to mouth-care products with enhanced bioadhesion. More specifically, the present invention is related to mouth-care products containing an effective amount of at least one polymer improving bioadhesion and other components suitable for mouth care products.

Bacteria that are present in the oral cavity lead to dental plaque formation. Plaque is considered to be the prime etiological factor in the development of caries, and it is also implicated in periodontal diseases. Plaque, when not sufficiently removed, develops into calculus, a hard, mineralised formation which deposits on the enamel surface of the teeth. There is also an association between the presence of calculus and the incidence of periodontal diseases. Serious teeth problems, like caries, gingivitis and other periodontal diseases, can be the result of formation of plaque and calculus.

In the prior art many different lines of approach have been used to find solutions to these problems in the field of oral care.

The first attempts were to remove plaque mechanically, using toothbrush and a dentrifice with polishing compounds. Abrasive and polishing compounds have many times been proposed to help the removal of plaque.

U.S. Pat. Nos. 3,927,201 and 3,927,202 describe dentifrice preparations comprising alkali metal phosphate salts as polishing agents. EP 0 097 476 describes β-phase calcium pyrophosphates as dentifrice abrasive. According to U.S. Pat. No. 4,340,583 also silicon dioxide compounds are suitable abrasive agents. U.S. Pat. No. 3,070,510 discloses dentifrice compositions comprising a resinous compound acting as an abrasive and U.S. Pat. No. 3,935,304 describes sodium bicarbonate.

Regular brushing aids in preventing a rapid build-up of plaque, but even regular brushing is not sufficient to remove all of the plaque which adhere to the teeth.

As plaque is developed by bacteria in the oral cavity, is has been proposed to use bactericides as antiplaque agents. The most important ingredient is chlorhexidine, described in many patents, for example DE 1 084 876. A disadvantage of this compound is the discoloration of the teeth. Compounds like bis-biguanides (U.S. Pat. No. 4,067,962) and alexidine (EP 0 004 719) did not stain the teeth, but proved to be insufficiently effective too. Examples of other bactericides are quaternary ammonium compounds, described in U.S. Pat. No. 4,323,551, sanquinarine (GB 2 042 336), Triclosan (5-chloro-2-(2,4-dichlorophenoxy)phenol) described in EP 0 161 899, p-aminobenzoic acid (U.S. Pat. No. 3,427,380) and many others. General enumerations of bactericides have been given in U.S. Pat. No. 5,178,851 and U.S. Pat. No. 5,180,578.

A reduction of the bacterial activity in the oral cavity is most important, as this activity is a major cause of most problems related to oral hygienic conditions.

Numerous attempts have been made to improve the effectivity, or substantivity, of the bactericides and the other active components of mouth care products, such as fluoride. These attempts were usually based on enhancing the bioadhesion of the active components in the mouth, by the addition of polymers to the products. The improved bioadhesion in the oral care products can be obtained by the use of polymers having an interaction with both the active substance and the glycoproteins (mucines). This may result in an enhanced substantivity, that is an improved availability, at the same time resulting in a prolonged retention time of the active component.

An example of a known polymer resulting in improved bioadhesion is Gantrez, a copolymer of maleic anhydride and methoxyvinyl. Another possible product is polyvinylpyrrolidone. Although these products initially lead to some improvement in the bioadhesion, it has been noted that after a short period of time the effect is diminished or even nullified. After even a short storage of a product containing both the aforementioned polymers and the active components, the active component or components crystallize, resulting therein that they are no longer active in the mouth.

It is an object of the invention to provide an oral care composition that renders improved bioadhesion and/or enhanced substantivity of at least some of the active components, such as bactericides. It is a further object to provide such a composition, which results in an improved fluoride uptake in the tooth enamel.

It was surprisingly found that the addition of one or more specific copolymers, optionally in combination with bactericide and/or a compound yielding fluoride ions, to mouthcare products leads to an effectively enhanced bioadhesion, even after prolonged time. Also a better fluoride uptake in the enamel was observed.

The present invention is therefore directed to a mouthcare product comprising an amount of at least one copolymer of N-vinylpyrrolidone and acrylic acid, in a weight ratio of 60-95 to 40-5, suitable additives and carrier material.

The present invention is also directed to a method to prevent the accumulation of dental plaque, thus reducing the formation of calculus and occurrence of caries, gingivitis and/or other periodontal diseases.

In a third aspect the present invention is directed to the use of a copolymer of N-vinylpyrrolidone and acrylic acid, in a weight ratio of 60-95 to 40-5, in mouth care products for improving the bioadhesion of bactericidal compounds and/ or an enhanced fluoride uptake, in mouth care products.

Surprisingly it has been found that the use of these specific copolymers results in a dramatic improvement of the substantivity of the therapeutic ingredients of oral care products. Especially the bioadhesion of bactericides is improved, compared to the known polymers as will be shown in the examples. Also the effect on the fluoride effectivity is pronounced.

The mouth care products of the present invention include the various known types of oral care products, such as tooth paste or cream, dental gel, tooth powder, mouth-wash, chewing gum, dental or chewing tablet, lozenge or effervescent tablet or any other suitable form.

These products include ingredients that are normally present in mouth care products, and also the specific copolymer to be used.

The copolymers to be used in the products of the invention are copolymers of N-vinylpyrrolidone and acrylic acid, whereby the weight ratio of the said monomers in the copolymer is to be within the range of 60-95 of N-vinylpyrrolidone to 40-5 of acrylic acid (hereinafter also referred to as VP-AA copolymer). Outside those ranges the effect of the improved bioadhesion does not occur, or only to a substantially lesser degree. A 50-50 copolymer does not have any effect and a homopolymer of N-vinylpyrrolidone does not have sufficient effect to be of any practical value. The vinylpyrrolidone in the copolymer is substantially not quaternised.

The copolymers can be prepared in a conventional manner, for example by random radical polymerisation in bulk, emulsion or suspension. The said copolymers are commercially available from ISP, under the trade name Acrylidone.

Copolymers having higher molecular weights tend to have a more pronounced effect. A lower limit for the molecular weight of the copolymer is generally 50,000, as lower molecular weights do not provide sufficient effect. Accordingly it is preferred to use products having a molecular weight of over 50,000. Upper limits of the molecular weight are governed by the production process and the requirement that the copolymer can be incorporated in the mouth care product. This means that it is preferred not to use molecular weights of over 1,000,000. Very suitable products have molecular weights of between 60,000 and 300,000. Those molecular weights refer to the viscosity average molecular weight, as defined in P. J. Flory, Principles of Polymer Chemistry, 1953, page 311-314.

The amount of copolymer to be used in the mouth care product ready for use may range between wide limits, namely between 0.01 and 5, preferably between 0.01 and 3%, calculated on the weight of the mouth care product. It is to be noted that in mouth care products that are in concentrated form, for example as concentrates that must be diluted prior to use, or in tablets to be dissolved, the concentration of the copolymer will be higher. Suitable amounts of copolymer for these products are between 2 and 50 wt. %.

These specific VP-AA copolymers are compatible with the usual mouth care products additives, such as fluorides, bactericides, abrasives, polishing agents, thickening agents, foaming agents, flavouring agents, sweeteners, preservatives and/or other basic ingredients.

According to a preferred embodiment of the invention the mouth care products also contain at least one bactericide. Suitable classes of bactericides to be used in the invention comprise the bisguanidine compounds, the phenolic compounds, metal salts, essential oils, plant extracts, surfactants, quaternary ammonium compounds and the lantibiotics. Examples of suitable, well known bactericides are given in U.S. Pat. No. 5,178,851 and U.S. Pat. No. 5,180,578, the contents of which is incorporated herein by reference. The use of lantibiotics has been disclosed in WO-A 94/05251, the contents of which is incorporated herein by reference.

In general all bactericides that are orally acceptable may be included in the mouth care products of the invention.

According to a preferred embodiment of the invention an effective amount of one or more lantibiotics is present in a mouth-care product, as the combination of a lantibiotic and the copolymer results in a synergistically improved effectivity of the mouth care product. Suitable amounts of lantibiotics are between 0.1 to 10,000 ppm. Preferably the upper total amount of the lantibiotics does not exceed 1000 ppm. The total amount will preferably be more than 1 but less than 500 ppm and will most preferably be in the range of between 1 and 250 ppm for tooth pastes and dental gels, and the total amount will preferably be in the range of between 1 and 100 ppm in the case of tablets, toothpowder's, mouth washes and lozenges.

Lantibiotics contain intrachain sulfide bridges, called lanthionine units, formed from the thioether groups of the amino acids lanthionine and β-methyllanthionine.

The lantibiotics which are useful in the mouth-care products according to the present invention are all presently known lantibiotics: nisin, subtilin, epidermin, gallidermin, pep 5, duramycin and duramycin B, cinnamycin, mersacidin, actagardin and ancovenin. These lantibiotics are described in Angew. Chem., Int. Ed. Engl., vol.30, no.9, 1053 (1991), but also other lantibiotics are expected to be suitable.

The preferred lantibiotics are nisin and subtilin; nisin is most preferred.

In the present invention it is advantageous to use the enzyme systems that are disclosed in U.S. Pat. Nos. 4,150,113 and 4,871,532. According to these patents, the contents of which is incorporated herein by reference, hydrogen peroxide producing enzym systems have advantageous effects on the reduction of oral bacterial activity. The most effective enzyme is the oxidoreductase enzyme glucose oxidase. This enzyme may be present in combination with other enzymes such as amyloglucosidase, dextranase and/or mutanase, optionally in the presence of zinc ion providing compounds and/or 8-hydroxyquinoline derivatives. Other enzymes like those disclosed in U.S. Pat. No. 4,152,418 may also be present.

Such combination of enzymes and copolymer has a combined advantageous effect on the oral cavity condition, i.e., it will lead to a reduction of the bacterial activity to diminish the deposition of dental plaque and calculus formation.

Other enzymes like lactoperoxidase, lactoferrin and lysozyme may also be present and provide a mouth care product having advantageous properties.

The presence of fluoride providing agents in the mouth-care products according to the present invention is important. The use of fluoride ions, or fluor-ion providing compounds as anti-caries agents is well known in the art. Surprisingly it has been found, that the combined use of copolymer and fluoride in the mouth care product results in a substantially improved incorporation of the fluoride in the tooth enamel, which improvement cannot be explained on the basis of adhesion alone. Accordingly the combination of copolymer and fluoride presumably results in an unexplained phenomenon, influencing the incorporation of fluoride in the enamel.

Suitable compounds may be slightly soluble in water or may be fully water-soluble. They are characterized by their ability to release fluoride ions in water and by freedom from undesired reaction with other compounds of the oral preparation. It was to be expected that the presence of fluoride would deactivate the lantibiotic. However, it has surprisingly been found that the combination of lantibiotic and fluoride enhances the effects against caries and gingivitis. Especially the use of alkalimetal fluorides, more in particular sodium fluoride, results in improved activity of the oral care products.

Among suitable compounds yielding fluoride ions are inorganic fluoride salts, such as soluble alkali metal and alkaline earth metal salts, for example sodium fluoride, potassium fluoride, barium fluoride, or calcium fluoride and ammonium fluoride, or a copper fluoride, or zinc fluoride, sodium fluorosilicate, ammonium fluorosilicate, sodium fluorozirconate, sodium mono-fluorophosphate, aluminium mono- and di-fluorophosphate, and fluorinated sodium calcium pyrophosphate. Alkali metal and tin fluorides, such as sodium and stannous fluorides, sodium monofluorophosphate, organic fluorides, such as aminfluoride and mixtures thereof, are preferred.

The amount of fluoride-providing compounds is dependent to some extent upon the type of compound, its solubility, and the type of oral preparation, but it must be a nontoxic, effective amount, generally about 0.005 to about 3.0% in the preparation, e.g. gel, tooth paste or tooth powder, an amount of such compound which releases up to about 5,000 ppm of F-ion by weight of the preparation is considered satisfactory. Any suitable minimum amount of such compound may be used, but it is preferable to employ sufficient compound to release about 300 to about 2,000 ppm, more preferably about 800 to about 1,500 ppm of fluoride ion. Typically, in the case of alkali metal fluorides and stannous fluoride, this component is present in an amount up to about 2% by weight, based on the weight of the preparation, and preferably in the range of about 0.05% to 1%. In the case of sodium monofluorophosphate, the compound may be present in an amount of about 0.1–3%. In dentrifrice preparations such as lozenges and chewing gum, the fluorine-providing compound is typically present in an amount sufficient to release up to about 500 ppm, preferably about 25 to about 300 ppm by weight of fluoride ion. Generally about 0.005 to about 1.0 wt % of such compound is present.

These products may contain the conventional components that are usually present in those products. The choice thereof depends on the actual type of product.

The mouth-care products according to the present invention can, if necessary, be based upon an orally acceptable vehicle.

In certain desirable forms of the present invention, the oral composition may be substantially solid or pasty in character, such as toothpowder, dental tablet, toothpaste or dental gel. Such solid or pasty oral preparations generally contains polishing material.

Examples of polishing materials are water-insoluble sodium metaphosphate, potassium metaphosphate, tricalcium phosphate, dehydrated calcium phosphate, anhydrous dicalcium phosphate, calcium pyrophosphate, magnesium orthophosphate, trimagnesium phosphate, aluminium oxide, aluminium oxide hydrate, calcium carbonate, aluminium silicate, zirconium silicate, silica, bentonite, and mixtures thereof. Silica based materials to be used in dentrifices are for example silica aerogels, pyrogels, xerogels, precipitated silica, amorphous silica, silicates and combinations thereof.

Other suitable polishing materials include the particulate thermosetting resins described in U.S. Pat. No. 3,070,510, such as melamine-phenolic-, and urea-formaldehydes, and cross-linked polyepoxides, polyesters and bicarbonates of sodium and/or potassium. Preferred polishing materials include silica having particle sizes of up to about 25 microns, a mean particle size of up 6–12 microns, silica gel or colloidal silica, and complex amorphous alkali metal aluminosilicate.

When visually clear gels are desired, a polishing agent of colloidal silica, such as xerogels and pyrogels are particularly useful, since they have refractive indices close to the refractive indices of gelling agent-liquid (including water and/or humectant) systems commonly used in dentifrice's.

The polishing material is generally present in the solid or paste compositions in weight concentrations of about 10% to about 99%. Preferably, it is present in amounts ranging from about 10% to about 75% in toothpaste, and from about 70% to about 99% in toothpowder.

In a toothpaste, the liquid vehicle may comprise water and humectant typically in an amount ranging from about 10% to about 90% by weight of the preparation. Glycerine, propylene glycol, sorbitol, polypropylene glycol and/or polyethylene glycol exemplify suitable humectants/carriers. Also advantageous are liquid mixtures of water, glycerine and sorbitol. In clear gels where the refractive index is an important consideration, about 3–30 wt % of water, 0 to about 80 wt % of glycerine, and about 20–80 wt % of sorbitol is preferably employed.

Toothpaste's and gels typically contain a natural or synthetic thickener or gelling agent in proportions of about 0.1 to about 10, preferably about 0.5 to about 5 wt %. A suitable thickener is synthetic hectorite, a synthetic colloidal magnesium alkali metal silicate complex clay available for example as Laponite (e.g. CP, SP 2002, D) marketed by Laporte Industries Limited.

Other suitable thickeners include Irish moss, gum tragacanth, starch, polyvinylpyrrolidone, poly (meth)acrylic acid, hydroxyethylpropyl cellulose, hydroxybutyl methyl cellulose, hydroxypropyl methyl cellulose, hydroxyethyl cellulose (e.g. available as Natrosol), sodium carboxymethyl cellulose, carragenan, Xanthan gum and colloidal silica.

Any suitable flavouring or sweetening material may also be employed. Examples of suitable flavouring constituents are flavouring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, APM (aspartyl phenyl alanine methyl ester), saccharine and the like. Suitably, flavour and sweetening agents may together comprise from about 0.1% to 5% or more of the preparation.

Other active components that may be used in the mouth care products of the present invention are phosphates, such as trimetaphosphates and diammoniumphosphates, enzymes, anti-tartar agents such as pyrophosphates, zinc-compounds and phosphonates and/or other anti-plaque ingredients, agents for sensitive teeth, wound healing agents, and specific ingredients as urea, xylitol, silicones and mixtures thereof. These components, as well as the amounts to be used, are known in the art. They are, where present, incorporated in the preparations in amounts which do not substantially adversely affect the properties and characteristics desired.

Anti-calculus agents can for example be chosen from pyrophosphate, zinc-compounds, diphosphonates and phosphocitrate.

Agents for sensitive teeth (dentin) are usually specific akalimetal salts, like strontium salts and potassium nitrate, -chloride or -citrate. Wound healing agents can for example be allantoin, chlorophyl, tocopherol and herbal extracts.

The vehicle or carrier in a tablet or lozenge is for example a non-cariogenic solid water soluble polyhydric alcohol (polyol) such as mannitol, xylitol, sorbitol, maltitol, a hydrogenated starch hydrolysate, Lycasin, hydrogenated glucose, hydrogenated disaccharide's, and hydrogenated polysaccharides, in an amount of about 90–98% by weight of the total composition. Solid salts such as sodium carbonate, sodium chloride, potassium bicarbonate or potassium chloride may totally or partially replace the polyol carrier.

Tableting lubricants, in minor amounts of about 0.1 to 5% by weight, may be incorporated into the tablet or lozenge formulation to facilitate the preparation of both the tablets and lozenges. Suitable lubricants include vegetable oils such as coconut oil, magnesium stearate, aluminium stearate, talc, starch and carbowax.

The compositions of the present invention can be incorporated in lozenges, or in chewing gum or other products, e.g. by stirring into a warm gum base or coating the outer surface of a gum base, illustrative of which may be mentioned jelutone, rubber latex, vinylite resins, etc., preferably with conventional plasticizers or softeners, sugar or other sweeteners or carbohydrates such as glucose, sorbitol and the like.

Lozenge formulations may optionally contain about 2% gum as barrier agent to provide a shiny surface as opposed to a tablet which has a smooth finish. Suitable non-cariogenic gums include the various carrageenans, carboxymethyl cellulose, alginate, guar gum, hydroxyethyl cellulose, Gantrez, and the like.

The lozenge or tablet may optionally be coated with a coating material such as waxes, shellac, carboxymethyl cellulose, alginate, guar gum, polyethylene maleic anhydride copolymer or Kappa-carrageenan to further increase the time it takes the tablet or lozenge to dissolve in the mouth. The uncoated tablet or lozenge is slow dissolving, providing a sustained release rate of the lantibiotic agent. Accordingly, the solid dose tablet and lozenge compositions of the present invention affords a relatively longer time period of contact of the teeth in the oral cavity with the active ingredient.

The mouth-care product according to the present invention can be prepared by the conventional ways of preparing said mouth-care products. The copolymer can be added to the finished mouth-care product or can be added during the production process. The process parameters like temperatures and pressures may have the conventional values.

The pH of the mouth care preparation of the invention in the form ready for use is generally in the range of from about 4.5 to about 10 and typically from about 5.5 to 9.

It is noteworthy that the compositions of the invention may be applied orally at the said pH ranges without substantially decalcifying or otherwise damaging dental enamel. The pH can be controlled with acid (e.g. citric acid or benzoic acid) or base (e.g. sodium hydroxide) or be buffered (e.g. with sodium citrate, benzoate, carbonate, or bicarbonate, disodium hydrogen phosphate, or sodium dihydrogen phosphate).

The invention will now be illustrated by means of the following examples. These examples are only used by way of illustration and are not intended to restrict the scope of the invention.

EXAMPLE 1

The degree of bioadhesion of a number of polymers was determined by the use of viscometric measurements, based on E. E. Hassan, J. M. Gallo, Pharmaceutical Research 7, 491 (1990). The experiments were performed with a Physica Rheometer (SM/MC 10, plate PP32) at 20° C.

A 20% porcine gastric mucin solution (ICN) was mixed with a 1% polymer solution in volume ratios of 2:1 and 1:1. The final pH was adjusted to 6.5, with NaOH. After determining the shear-force of the blank and the mixed solutions the degree of bio-adhesion was calculated using the following equation:

$F_b = F_t - F_m - F_p$ and $F = n.s$ (Pa)

$F_b$ = Force of bioadhesion $F_t$ = mixed solution $F_m$ = mucin solution $F_{p\_l}$ = polymer solution n = viscosity s = rate of shear ($s^{-1}$)

The force of bioadhesion was calculated (Ostwald) at a shear rate of 5000 $s^{-1}$.

The polymers used in this and other tests in the examples have been listed in the following table:

| Name | Type | Mol. Wt |
|---|---|---|
| Pemulen TR-1 | AA-co-AMA[3] | $1-3.10^6$ |
| Carrageenan XP 3172 | polysaccharide | $1-3.10^6$ |
| AVP-1 | AA-co-NVP[1] (25/75 w/w) | 250,000 |

-continued

| Name | Type | Mol. Wt |
|---|---|---|
| AVP-2 | AA-co-NVP[1] (50/50 w/w) | 250,000 |
| AVP-3 | AA-co-NVP[1] (75/25 w/w) | 250,000 |
| AVP-4 | AA-co-NVP[1] (25/75 w/w) | 80,000 |
| AVP-5 | AA-co-NVP[1] (75/25 w/w) | 80,000 |
| PVP 90 | NVP[2] | 630,000 |
| Gantrez S-97 | MA-MV[4] | 70,000 |
| Noveon | Acrylic acid | $1-4.10^6$ |
| CMC | carboxymethyl cellulose | $1-3.10^6$ |
| Xanthan gum | polysaccharide | $1-3.10^6$ |

[1]: acrylic acid-N-vinyl-2-pyrrolidone copolymer
[2]: N-vinyl-2-pyrrolidone homopolymer
[3]: acrylic acid-$C_{10-30}$ alkylmethacrylate
[4]: maleic anhydride-methoxyvinyl copolymer The results of the bioadhesion experiments are given in the following table:

| | F (Pa) at 5000 $s^{-1}$ | |
|---|---|---|
| Mucin/polymer | ratio 2:1 | ratio 1:1 |
| Pemulen TR-1 | 18.5 | 2 |
| Carrageenan XP 3172 | 0 | 6.5 |
| AVP-1 | 29 | 24.5 |
| AVP-2 | 10 | 7.5 |
| AVP-3 | 1.5 | 1.5 |
| PVP 90 | 40.7 | 14.5 |
| Gantrez S-97 | 21.5 | 29.5 |
| CMC | 43 | 40.5 |
| Xanthan gum | 35 | 15.5 |

EXAMPLE 2

Polymer and 3000 ppm bactericide (Bromochlorophene (BCP) or triclosan) were solved in distilled water at pH=12.5 (NaOH). Below pH=10.3 the bactericide precipitated to an extent dependent on the kind of polymer. The bactericide concentration was determined at pH 8, 7 or 6 in the supernatant solution by UV/VIS at pH=12.5 and 37° C.

| | ppm BCP in supernatant at pH | | |
|---|---|---|---|
| Polymer/BCP | 8 | 7 | 6 |
| Blank BCP (3000 ppm) | 119 | 36 | 4 |
| 0.5% AVP-1 | 354 ± 11 | 166 ± 4 | 46 ± 1 |
| 0.5% AVP-2 | 198 ± 5 | 10 ± 5 | 5 ± 3 |
| 0.5% AVP-3 | 27 ± 9 | — | — |
| 0.5% AVP-4 | 516 ± 1 | 135 ± 11 | 54 ± 9 |
| 0.5% PVP K25 | 2921 ± 259 | 2806 ± 306 | 2734 ± 344 |
| 0.5% PVP 120 | 2635 ± 2 | 2415 ± 28525 | 49 ± 6 |
| 0.5% Gantrez S-97 | 74 ± 72 | 1 ± 2 | 13 ± 1 |
| 0.25% Carrageenan XP3172 | 358 ± 91 | 313 ± 71 | 243± |
| 0.2% Noveon AA-1 | 52 ± 20 | 16 ± 10 | — |
| 0.2% Carbopol 974 P | 1 ± 1 | — | 2 ± 3 |
| 0.2% Xanthan gum | 51 ± 19 | 7 ± 4 | — |
| 0.2% CMC | 127 ± 4 | 75 ± 7 | 60 ± 2 |

The PVP's gave initially a high BCP retention, but this was not substantial due to continuous precipitation within a few hours.

| Polymer/triclosan | ppm triclosan in supernatant at pH | | |
|---|---|---|---|
| | 8 | 7 | 6 |
| Blank triclosan (3000 ppm) | 30 ± 2 | 15 ± 1 | 7 ± 3 |
| 0.5% AVP-1 | 2770 ± 163 | 2824 ± 36 | 2932 ± 76 |
| 0.5% AVP-4 | nd | 2705± | nd |
| 0.5% PVP 120 | 2240 ± 308 | 2073 ± 334 | 1898 ± 166 |
| 0.5% Gantrez S-97 | 106 ± 2 | 84 ± 2 | 74 ± 5 |
| 0.5% Carrageenan XP 3172 | 104 ± 1 | 81 ± 17 | 63 ± 3 |
| 0.5% CMC | 649 ± 20 | 28 ± 2 | 25 ± 2 |
| 0.25% Xanthan gum | 342 ± 2 | 370 ± 12 | 294 ± 4 |

The triclosan load in the PVP's as well as Gantrez S-97 was not substantial due to further precipitation in time (few hours for the PVP's and about 1 week for Gantrez S-97).

EXAMPLE 3

In vitro activity against oral-bacteria of bactericides (Bromochlorophene (BCP) and Triclosan) in combination with polymers The antibacterial activity of the various bactericides/polymers samples is shown by the following in vitro test.

Oral-bacteria Streptococcus mutans (C67-1) suspensions were prepared by growing the cells anaerobically at 37° C. overnight in Brain-Hart-Infusion-broth. The cells were centrifuged, washed and diluted in phosphate-peptone-buffer pH =7 (0.01M, 0.1% peptone).

The S. mutans suspension was brought into cups at 37° C. and mixed with 1% glucose. The metabolic activity of S. mutans was assessed by the acid forming. The inhibition of the metabolism after adding the BCP/Triclosan-polymer samples is the parameter of the antibacterial activity.

Inhibition of acid forming by S. mutans (C67-1) after adding the samples

| | % inhibition of acid forming | |
|---|---|---|
| | after 10 minutes | after 30 minutes |
| Triclosan sample bactericides/polymer | | |
| Propyleneglycol* (2.5%) | 9 | 9 |
| Triclosan/Propyleneglycol (25 ppm/2.5%) | 83 | 96 |
| PVP K25 (1%) | 0 | 0 |
| Triclosan/PVP 25 (25 ppm/0.005%) | 63 | 63 |
| Triclosan/PVP 25 (25 ppm/0.01%) | 63 | 63 |
| PVP K30 (1%) | 0 | 0 |
| Triclosan/PVP 30 (25 ppm/0.01%) | 60 | 60 |
| Triclosan/PVP 30 (25 ppm/0.01%) | 57 | 57 |
| Triclosan/PVP 30 (50 ppm/0.01%) | 57 | 57 |
| Triclosan/PVP 30 (50 ppm/0.02%) | 53 | 53 |
| AVP-4 (1%) | 23 | 50 |
| Triclosan/AVP-4 (25 ppm/0.005%) | 83 | 89 |
| Triclosan/AVP-4 (25 ppm/0.01%) | 80 | 80 |
| AVP-1 (1%) | 0 | 16 |
| Triclosan/AVP-1 (25 ppm/0.04%) | 83 | 87 |
| Gantrez S-97 (0.25%) | 64 | 94 |
| Triclosan/Gantrez (25 ppm/0.15%) | 48 | 70 |
| BCP sample bactericides/polymer | | |
| Propyleneglycol* (2.5%) | 18 | 18 |
| BCP/Propyleneglycol (50 ppm/5%) | 76 | 83 |
| PVP K25 (1%) | 0 | 0 |
| BCP/PVP 25 (50 ppm/0.01%) | 48 | 48 |
| BCP/PVP 25 (50 ppm/0.03%) | 58 | 58 |
| PVP K30 (1%) | 0 | 0 |
| BCP/PVP 30 (50 ppm/0.01%) | 60 | 60 |
| BCP/PVP 30 (50 ppm/0.03%) | 37 | 37 |
| AVP-4 (0.13%) | 0 | 10 |
| AVP-4 (1%) | 23 | 50 |
| BCP/AVP-4 (50 ppm/0.05%) | 73 | 80 |
| BCP/AVP-4 (50 ppm/0.13%) | 75 | 82 |
| AVP-1 (1%) | 0 | 16 |
| BCP/AVP-1 (100 ppm/0.25%) | 75 | 86 |

*Propyleneglycol is a solvent for Triclosan and BCP
*The samples Triclosan/BCP with polymers are soluble The results of this experiment show that acid-production by S. mutans is strongly lowered by adding BCP/Triclosan-polymers samples. The bactericides are active in combination with the above mentioned polymers. The metabolism of oral-bacteria S. mutans is inhibited by the bactericides/polymer samples and hence the accumulation of plaque on the teeth will be reduced as well.

EXAMPLE 4

Fluoride uptake experiments

Six different toothpaste formulations were prepared. To 40 ml 30% toothpaste supernatant solution thereof, 1 gram synthetic hydroxy apatite (Budenheim C73-08) was added. This solution was incubated at 37° C. under stirring (300 rpm) during 18 hours. The amount of CaF$_2$ (KOH) and FAP (HCl) was determined by measuring the fluoride concentration with an ion selective fluoride electrode.

The toothpaste formulation and the corresponding fluoride uptake has been given in the following table:

| Formula | A | B | C | D | E | F |
|---|---|---|---|---|---|---|
| Silica abrasive | 20 | 20 | 20 | 20 | 20 | 18 |
| Sorbitol (70%) | 31 | 31 | 33 | 33 | 33 | — |
| Glycerol (85%) | — | — | — | — | — | 45 |
| Water | 38 | 38 | 35 | 35 | 35 | 23 |
| NaF | 0.33 | 0.33 | 0.33 | 0.33 | 0.33 | 0.33 |
| Xanthan gum | — | 0.60 | 0.80 | 0.80 | 0.60 | 0.45 |
| CMC | 1.0 | — | — | — | — | — |
| Carbopol 954 | — | 0.20 | — | — | 0.40 | — |
| Gantez S-97 | — | — | — | 1.00 | — | — |
| AVP-1 | — | — | 1.00 | — | — | 1.00 |
| CaF$_2$ µg/g F$^-$ | 676 | 894 | 786 | 470 | 816 | 873 |
| (sd) | (98) | (194) | (133) | (106) | (21) | (108) |
| FAP µg/g F$^-$ | 1500 | 1584 | 1868 | 1384 | 2063 | 2283 |
| (sd) | (200) | (133) | (300) | (70) | (48) | (71) |

EXAMPLE 5

In vitro activity against oral-bacteria of nisin in combination with AVP-polymers Interaction of nisin with AVP-Polymers has been investigated with dialysis-tube-experiments. The dialysis-tube experiments results indicates that nisin has an interaction with AVP-polymers.

Human saliva was diluted 1:1 with phosphate peptone buffer pH 7 (0.01M, 0.1% peptone). The saliva suspension was brought into cups at 37° C., and mixed with 1% glucose. The metabolic activity of the oral microflora was assessed by the acid formation and ATP production. ATP stands for adenosine triphosphate, a compound containing a high-energy bond which is used by organisms to store the energy freed from catabolic processes. The ATP level is used as a measure of the bacterial activity in saliva.

| Nisin concentration in combination with polymer | acid formation | ATP |
|---|---|---|
| 0 | high | high |
| nisin 2 ppm + AVP-5 0.004% | strongly diminished | low |
| nisin 2 ppm + AVP-4 0.004% | strongly diminished | low |
| nisin 2 ppm + AVP-1 0.004% | strongly diminished | low |
| Standard nisin 2 ppm | strongly diminished | low |
| blank polymers AVP-5 0.004% | high | high |

This experiment illustrates that the addition of nisin/AVP-polymers samples restrains the acid formation and reduces the ATP level in the saliva. From this it appears that nisin is active in combination with the above mentioned AVP-polymers. The addition of nisin/AVP-polymers thus lowers the metabolic activity of the oral bacteria and hence the accumulation of plaque on the teeth will be reduced as well.

EXAMPLE 6

Inhibition of the enzymatic hydrolysis of pyrophosphate

To a solution, 3 ml, containing 480 ppm of pyrophosphate, various polymers, as defined in the table, optionally in combination with fluoride, and tris buffer (pH=7), $6*10^{-2}$ U acid phosphatase and $4*10^{-2}$ U pyrophosphatase ware added. The enzymatic hydrolysis of pyrophosphatase was determined by the withdrawal of 0.5 ml samples and measuring the orthophosphate concentration (V/MO complex). The results after various intervals have been given in the table.

| | ppm orthophosphate after (min) | | |
|---|---|---|---|
| | 60 | 120 | 240 |
| blank | 20.3 | 69.4 | 150.5 |
| NaF | 1.8 | 3.9 | 9.6 |
| Gantrez S-97 | 1.8 | 8.9 | 23.8 |
| Carbopol 954 | 2.5 | 6.8 | 18.2 |
| AVP-1 | 0 | 0 | 0 |
| F⁻/Gantrez S-97 | 1.1 | 4.6 | 11.0 |
| F⁻/Carbopol 954 | 1.1 | 3.9 | 12.5 |
| F⁻/AVP-1 | 0 | 0 | 0 |

These experiments show that the polymer AVP-1 effectively inhibits the enzymatic hydrolysis of pyrophosphate.

EXAMPLE 7

Dentifrices

| | A | B | C | D |
|---|---|---|---|---|
| Silica abrasive | 20 | 20 | 20 | 20 |
| Glycerol (85%) | 10 | 45 | 10 | 5 |
| Sorbitol (70%) | 20 | — | 20 | 20 |
| Xanthan gum | 0.8 | 0.8 | 0.8 | — |
| NaF | 0.24 | 0.33 | 0.33 | 0.24 |
| MFP (20%) | 1.40 | — | — | 1.40 |
| Ortho phosphate | 1 | 1 | 1 | — |
| Sodium Lauryl Sulfate | 2 | 2 | 2 | 2 |
| Bromochlorophene | 0.3 | — | 0.3 | — |
| AVP-1 | 1.5 | 1.0 | 1.5 | 1.0 |
| Calcium citrate | 0.5 | — | 0.5 | — |
| Sodium trimetaphosphate | 0.25 | — | 0.25 | 1.0 |
| Aroma | 0.6 | 0.6 | 0.6 | 0.6 |
| Sodium benzoate | — | 0.1 | — | 0.1 |
| Xylitol | — | — | 10 | — |
| Sodium/Potassium Pyrophosphate | — | — | — | 5.8 |
| Propylene Glycol | — | — | — | 5 |
| NaCMC | — | — | — | 1.7 |
| Water | ad 100 | ad 100 | ad 100 | ad 100 |

EXAMPLE 8

Mouthwash

| Glycerol | 10 |
|---|---|
| Sorbitol | 10 |
| Propylene glycol | 2.5 |
| SDS-SLS | 0.2 |
| NaF | 0.05 |
| AVP-1 | 1 |
| Aroma | 0.1 |
| BCP | 0.3 |
| Water | to 100 |

EXAMPLE 9

Toothpaste

A toothpaste is prepared according to the method known in the art and consists of the following components: (all amounts are percent by weight unless otherwise indicated).

| Glycerol | 15.0 |
|---|---|
| Aluminium oxide hydrate | 35.0 |
| Ethoxylated fatty alcohol | 3.0 |
| Carraghene | 1.75 |
| Esters of para-hydroxy-benzoic acids (PHB) | 0.15 |
| Aroma | 1.2 |
| Sodium fluoride | 0.33 |
| Nisin | 250 ppm |
| AVP-1 | 1.5 |
| Water | to 100% |

EXAMPLE 10

Mouthwash

A mouthwash is prepared according to the method known in the art and consists of the following components: (all amounts are percent by weight unless otherwise indicated).

| Glycerol | 15.0 |
|---|---|
| Xylitol | 15.0 |
| Aroma | 0.05 |
| Tween 80 | 2.0 |
| Propyl para hydroxy benzoate | 0.1 |
| Sodium citrate | 0.2 |
| Sodium fluoride | 0.1 |
| Nisin | 100 ppm |
| AVP-1 | 2.0 |
| Water | to 100% |

EXAMPLE 11

Lozenge

A lozenge is prepared according to the method known in the art and consists of the following components: (all amounts are in mg unless otherwise indicated).

| Sorbitol | 1500 |
| --- | --- |
| Encapsulated aroma | 10 |
| Sodium stearate | 10 |
| Phosphate buffer pH = 5.5 | 50 |
| Poly vinyl pyrrolidone (PVP) | 20 |
| Sodium fluoride | 1.0 |
| AVP-1 | 1000 |
| Nisin | 100 ppm |

EXAMPLE 12

Chewing tablet

A chewing tablet is prepared according to the method known in the art and consists of the following components (all amounts are in percent by weight unless otherwise indicated).

| Gum base | 25 |
| --- | --- |
| Sorbitol | 17.5 |
| Mannitol | 5 |
| Aroma | 0.5 |
| Glycerol | 3.0 |
| Xylitol | 10 |
| Sodium fluoride | 0.01 |
| Nisin | 50 ppm |
| AVP-1 | 0.5 |
| Sorbitol | to 100% |

EXAMPLE 13

Effervescent tablet

An effervescent tablet is prepared according to the method known in the art and consists of the following components: (all amounts are in mg unless otherwise indicated).

| Sodium carbonate | 40 |
| --- | --- |
| Citric acid | 20 |
| Poly vinyl pyrrolidone (PVP) | 2 |
| Sorbitol | 24 |
| Encapsulated aroma | 2 |
| Sodium fluoride | 10 |
| Subtilin | 250 ppm |
| AVP-1 | 500 |
| dissolve in: 15 ml water | |

EXAMPLE 14

Tooth powder

A tooth powder is prepared according to the method known in the art and consists of the following components: (all amounts are in percent by weight unless otherwise indicated).

| Aroma | 2 |
| --- | --- |
| Sodium saccharinate | 0.15 |
| Detergent | 1 |
| Sodium fluoride | 0.33 |
| Nisin | 100 ppm |
| AVP1 | 4 |
| Calcium phosphate | to 100% |

EXAMPLE 15

Toothpaste

A toothpaste is prepared according to the method known in the art and consists of the following components: (all amounts are in percent by weight unless otherwise indicated).

| Sorbitol | 22 |
| --- | --- |
| Silica | 22 |
| Ethoxylated fatty alcohol | 3.0 |
| Carraghene | 1.5 |
| Sodium benzoate | 0.1 |
| Aroma | 0.6 |
| Sodium saccharinate | 0.1 |
| Amyloglucosidase | 18 U/g |
| Glucose oxidase | 6 U/g |
| Mutanase | 16 U/g |
| Zinc gluconate | $8.10^{-4}$ |
| 5 chloro-8-hydroxyquinoline | $1.10^{-3}$ |
| Sodium fluoride | 0.33 |
| Subtilin | 150 ppm |
| AVP-1 | 1 |
| Water | to 100% |

We claim:

1. A mouth care product in the form of a tooth paste, a tooth cream, a dental gel, a tooth powder, a mouth-wash, a chewing gum, a concentrate, a dental tablet, a chewing tablet, a lozenge, or an effervescent table, the mouth care product comprising:

an amount of at least one copolymer of N-vinylpyrrolidone and acrylic acid, in a weight ratio of 60-95 to 40-5; and an abrasive agent, a polishing agent, a thickening agent, a colouring agent, a sweetening agent, a flavouring agent, a foaming agents, another active component, or a combination thereof.

2. A mouth care product according to claim 1, wherein the weight ratio of the at least one copolymer of N-vinylpyrrolidone and acrylic acid is in the range of about 65:35 to 95:5.

3. A mouth care product according to claim 1, wherein the amount of said copolymer is between 0.01% and 5% by weight of the product.

4. A mouth care product according to claim 2, wherein the amount of said copolymer is between 0.01% and 3% by weight of the product.

5. A mouth care product according to claim 1 in the form of a concentrate or a tablet, wherein the amount of said copolymer is between 2 and 50 wt. % of the said concentrate or tablet.

6. A mouth care product according to claim 1, further comprising a bactericidal component.

7. A mouth care product according to claim 6, wherein the bactericidal component is a lantibiotic, triclosan, hexachlorophene, bromochlorophene, or nisin.

8. A mouth care product according to claim 6, wherein the bactericidal component is present in the product ready for use in an amount between 0.1 and 10,000 ppm.

9. A mouth care product according to claim 1, further comprising a fluoride source.

10. A mouth care product according to claim 9, wherein the fluoride source is alkalimetal fluoride, monofluorphosphate, or tin (II) fluoride.

11. A mouth care product according to claim 9 wherein the fluoride source is present in an amount sufficient to release 30 to 2,000 ppm of fluoride ion in the product ready for use.

12. A mouth care product according to claim 9, further comprising a bactericidal compound.

13. A mouth care product according to claim 12, wherein the bactericidal compound is nisin.

14. A method for preparing a mouth care product in the form of a tooth paste, a tooth cream, a dental gel, a tooth powder, a mouth-wash, a chewing gum, a concentrate, a dental tablet, a chewing tablet, a lozenge, or an effervescent table, the method comprising:

incorporating into the mouth care product a copolymer of N-vinylpyrrolidone and acrylic acid, in a weight ratio of 60-95 to 40-5.

15. A method for improving the bioadhesion of a bactericidal compound in a mouth care product, the method comprising:

incorporating into the mouth care product a copolymer of N-vinylpyrrolidone and acrylic acid, in a weight ratio of 60-95 to 40-5;

wherein the mouth care product is in the form of a tooth paste, a tooth cream, a dental gel, a tooth powder, a mouth-wash, a chewing gum, a concentrate, a dental tablet, a chewing tablet, a lozenge, or an effervescent table.

16. A method for reducing occurrence of caries, gingivitis, or other periodontal disease, the method comprising:

applying orally a mouth-care product comprising a copolymer of N-vinylpyrrolidone and acrylic acid, in a weight ratio of 60-95 to 40-5;

wherein the mouth care product is in the form of a tooth paste, a tooth cream, a dental gel, a tooth powder, a mouth-wash, a chewing gum, a concentrate, a dental tablet, a chewing tablet, a lozenge, or an effervescent table.

17. A method according to claim 16, wherein the mouth care product further comprises an effective amount of at least one lantibiotic, an effective amount of at least one compound providing fluoride ions, or a combination thereof.

* * * * *

UNITED STATES PATENT AND TRADEMARK OFFICE
CERTIFICATE OF CORRECTION

PATENT NO. : 5,670,138

DATED : SEPTEMBER 23, 1997

INVENTOR(S) : VENEMA ET AL.

It is certified that error appears in the above-identified patent and that said Letters Patent is hereby corrected as shown below:

Title page, under Foreign Application Priority Data, "94201962" should read —94201962.1—.

Column 1, line 23, "dentrifice" should read —dentifrice—.

Column 1, line 38, "is" should read —it—. (second occurrence)

Column 4, line 7, "enzym" should read —enzyme—.

Column 5, line 9, "dentrifrice" should read —dentifrice—.

Column 5, line 33, "dentrifices" should read —dentifrices—.

Column 7, line 54, "$F_{p-1=polymer\ solution}$" should read —$F_p$=polymer solution—.

Column 10, line 46, "Gantez S-97" should read —Gantrez S-97—.

Column 11, line 28, "ware" should read —were—.

Column 14, line 23, "table" should read —tablet—.

Column 15, line 3, "table" should read —tablet—.

UNITED STATES PATENT AND TRADEMARK OFFICE
CERTIFICATE OF CORRECTION

PATENT NO. : 5,670,138

DATED : SEPTEMBER 23, 1997

INVENTOR(S) : VENEMA ET AL.

It is certified that error appears in the above-identified patent and that said Letters Patent is hereby corrected as shown below:

Column 15, line 16, "table" should read —tablet—.

Column 16, line 10, "table" should read —tablet—.

Signed and Sealed this

Twenty-fourth Day of August, 1999

Attest:

Q. TODD DICKINSON

*Attesting Officer*    *Acting Commissioner of Patents and Trademarks*